US010117939B2

(12) United States Patent
Akbarieh et al.

(10) Patent No.: US 10,117,939 B2
(45) Date of Patent: Nov. 6, 2018

(54) PHARMACEUTICAL COMPOSITIONS COMPRISING NEBIVOLOL OR A NEBIVOLOL ANALOGUE

(71) Applicant: MYLAN PHARMACEUTICALS ULC, Calgary (CA)

(72) Inventors: Mostafa Akbarieh, Richmond Hill (CA); Fazal M. Mohideen, Pickering (CA); Shetal Shah, Toronto (CA)

(73) Assignee: Mylan Pharmaceuticals ULC (CA)

( * ) Notice: Subject to any disclaimer, the term of this patent is extended or adjusted under 35 U.S.C. 154(b) by 0 days.

(21) Appl. No.: 14/704,375

(22) Filed: May 5, 2015

(65) Prior Publication Data

US 2015/0231261 A1    Aug. 20, 2015

Related U.S. Application Data

(63) Continuation of application No. 12/523,686, filed as application No. PCT/CA2008/000119 on Jan. 22, 2008.

(30) Foreign Application Priority Data

Jan. 22, 2007  (CA) .................................... 2575527

(51) Int. Cl.

| A01N 43/42 | (2006.01) |
| A61K 31/44 | (2006.01) |
| A01N 43/50 | (2006.01) |
| A61K 31/415 | (2006.01) |
| A61K 47/38 | (2006.01) |
| A61K 31/353 | (2006.01) |
| A61K 47/26 | (2006.01) |
| A61K 47/36 | (2006.01) |
| A61K 47/02 | (2006.01) |
| A61K 47/12 | (2006.01) |
| A61J 3/10 | (2006.01) |

(52) U.S. Cl.
CPC ............ *A61K 47/38* (2013.01); *A61J 3/10* (2013.01); *A61K 31/353* (2013.01); *A61K 47/02* (2013.01); *A61K 47/12* (2013.01); *A61K 47/26* (2013.01); *A61K 47/36* (2013.01)

(58) Field of Classification Search
CPC ...................................................... A61K 31/33
USPC ................................................. 514/183, 170
See application file for complete search history.

(56) References Cited

U.S. PATENT DOCUMENTS

| 5,338,732 A | 8/1994 | Atzinger et al. |
| 5,759,580 A | 6/1998 | Jans et al. |
| 6,410,054 B1 | 6/2002 | Thosar et al. |
| 2003/0114461 A1 | 6/2003 | Galli et al. |
| 2007/0259950 A1 | 11/2007 | Sheth et al. |

FOREIGN PATENT DOCUMENTS

| CA | 2182582 | 8/1995 |
| EP | 0 145 067 | 6/1985 |
| EP | 0 334 429 | 9/1989 |
| EP | 0 744 946 | 8/1995 |
| EP | 1 839 658 | 10/2007 |
| JP | H09-008913 | 9/1997 |
| WO | WO 1995/022325 | 8/1995 |
| WO | WO 2005/099699 | 10/2005 |
| WO | WO 2005/117899 | 12/2005 |
| WO | WO 2006/025070 | 3/2006 |
| WO | WO 2006/084684 | 8/2006 |
| WO | WO 2006/130174 | 12/2006 |

OTHER PUBLICATIONS

Requisition by the Examiner corresponding to Canadian Patent Application No. 2,675,538, dated Dec. 2, 2015.
Decision of Rejection corresponding to Japanese Patent Application No. 2009-546620, dated Jul. 16, 2013, with English translation.
Extended European Search Report corresponding to European Patent Application No. 08706266, dated Jul. 12, 2013.
International Preliminary Report on Patentability corresponding to International Patent Application No. PCT/CA2008/000119, dated Jul. 28, 2009.
International Search Report corresponding to International Patent Application No. PCT/CA2008/000119, dated Apr. 30, 2008.
Lachman et al. (1990) *Pharmaceutical Dosage Forms: Tablets.* 2nd Ed. vol. 2. Marcel Dekker, Inc. New York, New York. p. 7.
Lachman et al. (1990) *Pharmaceutical Dosage Forms: Tablets.* 2nd Ed. vol. 2. Marcel Dekker, Inc. New York, New York. p. 35.
Liebermann et al. (1996) *Pharmaceutical Dosage Forms: Disperse Systems.* 2nd Ed. vol. 1. Marcel Dekker, Inc. New York, New York. p. 261.
Liebermann et al. (1996) *Pharmaceutical Dosage Forms: Disperse Systems.* 2nd Ed. vol. 1. Marcel Dekker, Inc. New York, New York. p. 107.
McNeely et al. (1999) "Nebivolol in the Management of Essential Hypertension: A Review," *Drugs.* 57(4):633-651.
Notice of Reasons for Rejection corresponding to Japanese Patent Application No. 2009-546620, dated Nov. 27, 2012.
Requisition by the Examiner corresponding to Canadian Patent Application No. 2,675,538, dated May 30, 2014.
Swenson et al. (Aug. 1994) "Intestinal Permeability Enhancement: Efficacy, Acute Local Toxicity, and Reversibility," *Pharm Res* 11(8):1132-1142.
Van Peer et al. (1991) "Clinical Pharmacokinetics of Nebivolov: A Review," *Drug Investigation.* 3:25-30.
Examination Report corresponding to Australian Patent Application No. 2008209264, dated Feb. 6, 2013.
Requisition by the Examiner corresponding to Canadian Patent Application No. 2,675,538, dated Feb. 19, 2015.
Examination Report corresponding to European Patent Application No. 08706266, dated May 7, 2014.
B. J. Ennis (2005) "Theory of Granulation: An Engineering Perspective," in Handbook of Pharmaceutical Granulation, 2nd Edition, D.M. PArith (ed), Francis & Taylor (Boca Raton, FL, US.

*Primary Examiner* — Layla Soroush

(57) ABSTRACT

The present application provides pharmaceutical compositions comprising as the active medicinal ingredient nebivolol, a nebivolol analog or a pharmaceutically acceptable acid addition salt thereof and a wetting agent. The invention also relates to methods of preparing and using said compositions.

5 Claims, No Drawings

PHARMACEUTICAL COMPOSITIONS COMPRISING NEBIVOLOL OR A NEBIVOLOL ANALOGUE

CROSS REFERENCE TO RELATED APPLICATIONS

This application is a continuation of U.S. Ser. No. 12/523,686, filed Dec. 22, 2009. U.S. Ser. No. 12/523,686 is a national stage application under 35 U.S.C. § 371 of PCT/CA08/00119, filed Jan. 22, 2008, which claims the benefit of Canadian Patent Application No. 2,575,527, filed Jan. 22, 2007, each of which applications is incorporated by reference in its entirety herein.

FIELD OF THE INVENTION

The present invention pertains to the field of pharmaceutical compositions and methods of preparation thereof and, more particularly, to pharmaceutical compositions comprising, as the active medicinal ingredient, nebivolol, a nebivolol analogue or a pharmaceutically acceptable salt thereof and a wetting agent, and to a method of preparation thereof.

BACKGROUND OF THE INVENTION

Nebivolol is the generic name of ((±))-(R*(S*(S*—(S*))))-(alpha),(alpha)'-(iminobis(methylene)bis-(6-fluoro-3,4-dihydro-2H-1-benzopyran-2-methanol). The general structure of nebivolol as it's hydrochloride salt is shown as Formula (a).

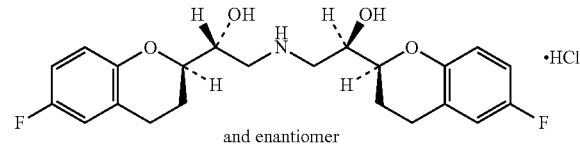

Formula (a)

and enantiomer

Nebivolol is a ß1-adrenoceptor blocking drug, or ß-blocker, distinguished from other members of its drug class by its additional nitric oxide (NO)-mediated vasodilatory effects. Consequently, as well as effectively lowering blood pressure by blocking ß1-adrenoceptors in the heart and vasculature, nebivolol may also slow or prevent some of the vascular complications associated with hypertension, by improving arterial compliance and reducing peripheral vascular resistance. Nebivolol is described as a mixture of equal amounts of 2 enantiomers having respectively the SRRR- and the RSSS-configuration. The SRRR-configuration is a potent and selective ß1-adrenergic antagonist both in vitro and in vivo. Nebivolol can be distinguished from other ß-adrenergic antagonists because it acutely lowers blood pressure in spontaneously hypertensive rats, decreases total peripheral vascular resistance and augments stroke volume in anaesthetized dogs. These haemodynamic effects are largely attributable to the RSSS-configuration of nebivolol. It was also discovered that RSSS-nebivolol is a potentiator for a series of antihypertensive agents such as atenolol, propanolol, prazosin, hydralazine and, interestingly, also its own enantiomer, i.e., the SRRR-configuration. Several clinical trials have also demonstrated the therapeutic potential of nebivolol as a ß1-selective beta-blocker and antihypertensive agent.

Nebivolol as it's hydrochloride salt is available in a tablet dosage form and sold in the UK as Nebilet® for the treatment of mild to moderate essential hypertension in humans.

Methods of preparing Nebivolol and pharmaceutically acceptable salts are described generally in EP 0 145 067 and more specifically in EP 0 334 429 which are incorporated herein by reference.

EP 0 145 067 generally describes 2,2'-iminobisethanol derivatives useful for the treatment and/or prevention of disorders of the coronary vascular system.

EP 0 334 429 describes (iminobismethylene)bis(3,4-dihydro-2H-1-benzopyran-2-methanol) derivatives including nebivolol and pharmaceutically acceptable salts.

As Nebivolol has basic properties it may be converted into its pharmaceutically acceptable acid addition salt forms by treatment with appropriate acids. Appropriate acids are, for example, inorganic acids, such as the hydrochloride or hydrobromide.

EP 0 744 946 B1 by Eugeen et al, incorporated herein by reference, discloses suitable solid and semi-solid pharmaceutical compositions comprising inter alia nebivolol and pharmaceutically acceptable salts for use as antihypertensive agents. Dosage forms include powders, pills, capsules, tablets, suppositories, creams, gels, ointments. Tablets are a particularly preferred solid oral dosage form. The specification describes that oral administration of nebivolol hydrochloride was impeded by the poor dissolution when in a "normal" crystalline form.

A very important factor influencing the bioavailability of active ingredients after oral administration is the dissolution or, more particularly, the rate of dissolution of the active ingredient or drug substance, particularly in gastric fluid. It is recognized in the art that the dissolution for solid dosage forms, particularly tablets, should amount to at least 75% in 45 minutes in 0.1 M Hydrochloric acid at a temperature of 37° C. as measured according to test procedures described in the official pharmacopoeias known to those skilled in the art, e.g., the U.S. Pharmacopoeia XXII.

Investigations towards improving the dissolution and bioavailability of nebivolol hydrochloride led to compositions prepared using nebivolol hydrochloride having a reduced particle size (EP 0 744 946). However the inventors found that after performing a comparative dissolution test comparing the extent of dissolution of "normal" crystalline material with "micronized" nebivolol hydrochloride, the dissolution of the micronized material was described as even worse than material in the normal crystalline form. EP 0 744 946 teaches that the specific area of the micronized material is at least about $23 \times 10^3$ cm$^2$/g ($2.3 \times 10^3$ m$^2$/kg), preferably more than $25 \times 10^3$ cm$^2$/g ($2.5 \times 10^3$ m$^2$/kg), more preferably more than $28 \times 10^3$ cm$^2$/g ($2.8 \times 10^3$ m$^2$/kg), and most preferably more than $31 \times 10^3$ cm$^2$/g ($3.1 \times 10^3$ m$^2$/kg). Alternatively the micronized material was described in the following way; at most 50% of the particles may have a diameter larger than 10 μm, i.e. the $DL_{50}$ has a maximum value of 10 μm. Preferably the $DL_{50}$ should amount to less than 8 μm. At most 10% of the particles may have a diameter larger than 20 μm, i.e. the $DL_{10}$ has a maximum value of 20 μm. Preferably the $DL_{10}$ should amount to less than 18 μm.

Following investigation, the dissolution characteristics of nebivolol hydrochloride in an oral dosage form were apparently improved by formulating micronized material with a wetting agent where the ratio (w/w) of wetting agent/active ingredient ranged between 0.025 and 0.5.

Hence, in summary, the invention disclosed in EP 0 744 946 emphasized that in order to achieve the required pharmacopoeial dissolution, the nebivolol hydrochloride needed to be micronized and sufficiently wet. Wetting was achieved through the inclusion of a wetting agent within the aforesaid ratio. This ratio was described as being an important factor because on the one hand the percentage level of wetting agent needs to be sufficient to influence the desired dissolution but not at the expense of undesirable tablet hardness that affects production on a commercial scale. When the level of wetting agent is too high, resulting tablets do not have the appropriate hardness. Additionally it is known in the art that high levels of wetting agents in pharmaceutical formulations are linked to undesirable effects in humans e.g. permeability enhancement and local damage are closely related sequele of the interaction of surfactants with the intestinal wall (Swenson E S et al; Pharm Res 1994 Aug. 11(8) p 1132-42). Ingested wetting agents may influence the penetration of potentially toxic compounds (Liebermann H. A. et al Pharmaceutical Dosage Forms: Disperse Systems, $2^{nd}$ Ed, Vol 1, page 261).

"Micronization" as used herein is a generic term for the process where the mean particle size of a particular drug substance is reduced by mechanical means which increases the surface area of the particles available for contact with biological fluids. Micronization can be carried out by known techniques such as milling or sieving through appropriate sieves; see Pharmaceutical Dosage Forms: Vol 2, 1990; H A Lieberman, page 107. However, these techniques are time consuming and uneconomic when the objective is to prepare pharmaceutical dosage forms comprising nebivolol hydrochloride on a commercial scale that also complies with rigorous internal and external quality control requirements.

Furthermore the known processes of micronization may be unsuitable for thermolabile or physically unstable drug substances leading to undesirable degradation of the material under investigation. Fine powder particles also create potentially dangerous dust conditions which require operators to wear respirators for safe handling; Lachman & Liebrman, Pharmaceutical Dosage Forms: Tablets, Vol 2, second edition, 1990, page 35.

WO 2006/025070 to Sheth R et al and incorporated herein discloses inter alia pharmaceutical compositions comprising nebivolol hydrochloride e.g., tablets and capsules without using a wetting agent.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a pharmaceutical composition comprising nebivolol or a nebivolol analogue. Thus, in accordance with a first aspect of the present invention, there is provided a pharmaceutical composition for oral administration comprising an active ingredient and a wetting agent, wherein the active ingredient is nebivolol, a nebivolol analogue or a pharmaceutically acceptable salt thereof, the wetting agent is not colloidal silicon dioxide and the ratio (w/w) of wetting agent to active ingredient is less than 0.025.

In a preferred embodiment, the pharmaceutical composition is characterized in that the pharmaceutically acceptable salt of nebivolol is the hydrochloride salt.

In another preferred embodiment, the pharmaceutical composition is characterized in that the nebivolol hydrochloride is unmicronized.

In another preferred embodiment, the pharmaceutical composition is characterized in that the wetting agent consists of a polysorbate.

In another preferred embodiment the pharmaceutical composition is characterized in that the polysorbate is polysorbate 80.

In another preferred embodiment, the pharmaceutical composition is characterized in that the pharmaceutically acceptable carrier is selected from; a filler, a binder, a disintegrant, a lubricant and a glidant or mixtures thereof.

In another preferred embodiment, the pharmaceutical composition is characterized in that the pharmaceutically acceptable salt of nebivolol is the hydrochloride salt, the wetting agent is polysorbate 80, the filler is a spray dried mixture of microcrystalline cellulose and lactose and/or lactose monohydrate, the binder is hydroxypropylmethylcellulose, the disintegrant is corn starch and/or croscarmellose sodium, the lubricant is magnesium stearate and the glidant is colloidal silicon dioxide.

In another preferred embodiment, the pharmaceutical composition comprises, on a weight percentage basis, from about 0.5% to about 10% of nebivolol or a pharmaceutically acceptable salt, from about 0.01% to about 0.04% of a wetting agent, from about 20% to about 80% of a filler, from about 1% to about 4% of a binder, from about 2% to about 30% of a disintegrant, from about 0.25% to about 2% of a lubricant and from about 0.1% to about 2% of a glidant.

In another preferred embodiment the pharmaceutical composition is in the form of a tablet.

In another preferred embodiment the pharmaceutical composition in the form of a tablet exhibits a dissolution of at least 75% after 45 minutes.

According to a second aspect of the present invention, there is provided a process for the preparation of a pharmaceutical composition for oral administration comprising an active ingredient and a wetting agent, wherein the active ingredient is nebivolol, a nebivolol analogue or a pharmaceutically acceptable salt thereof, the wetting agent is not colloidal silicon dioxide and the ratio (w/w) of wetting agent to active ingredient is less than 0.025. In a preferred embodiment, the process comprises: (a) combining the active ingredient in intimate admixture with one or more pharmaceutically acceptable carriers; and (b) optionally compressing the mixture from step (a) into a tablet.

In another preferred embodiment, step (a) of the process includes wet granulation.

According to a third aspect of the present invention, there is provided a use of a pharmaceutical composition comprising nebivolol or a pharmaceutical composition for oral administration comprising an active ingredient and a wetting agent, wherein the active ingredient is nebivolol, a nebivolol analogue or a pharmaceutically acceptable salt thereof, the wetting agent is not colloidal silicon dioxide and the ratio (w/w) of wetting agent to active ingredient is less than 0.025, for the treatment of coronary vascular disorders in humans.

DETAILED DESCRIPTION OF THE INVENTION

The person skilled in the art of developing pharmaceutical compositions comprising nebivolol hydrochloride is faced with the dual problem of ensuring nebivolol has an acceptable dissolution in biological media whilst at the same time ensuring the composition facilitates production on an industrial scale and can satisfy the rigorous requirements of internal and external quality control.

Surprisingly, the present inventors have developed compositions that meet these objectives and that solve the hitherto known drawbacks of dissolution of nebivolol hydrochloride by using a lower ratio of wetting agent to active ingredient than employed in EP 0 744 946. Moreover, it was surprisingly found that as a result of the use of the lower ratio of wetting agent to active ingredient it was not necessary to micronize the active ingredient, thereby making the composition and process for production more economical.

Through thorough investigations and trials, the inventors have found that oral dosage forms comprising nebivolol, nebivolol analogues, or pharmaceutically acceptable salts thereof, can be prepared which exhibit excellent dissolution in compliance with pharmacopoeial standards known to those in the art using a wetting agent, where the ratio (w/w) of wetting agent/active ingredient is less than 0.025. This is particularly demonstrated herein using pharmaceutical compositions comprising nebivolol hydrochloride as the active ingredient.

The present inventors have now found that the percentage by weight of the wetting agent per dose is critical to the invention and it is this aspect in particular which distinguishes the invention from compositions known in the art.

Active Ingredient

The active ingredient in the compositions of the present invention is nebivolol, a nebivolol analogue or a pharmaceutically acceptable salt thereof. As used in the present application, the term "nebivolol analogue" refers to compounds that are structurally similar to nebivolol and exhibit a similar pharmaceutical activity. Preferably, the nebivolol analogue is ß receptor antagonist. Examples of nebivolol analogues that are suitable for incorporation in the composition of the present invention include, but are not limited to, metipranolol, nadolol, oxprenolol, penbutolol, pindolol, propanolol, tertatolol, timolol, sotalol, atenolol, acebutolol, celiprolol, betaxolol, bisoprolol, esmolol and metoprolol. The present invention is particularly described using reference to nebivolol hydrochloride, however, a worker skilled in the art would readily appreciate that the present invention is not limited to compositions containing nebivolol hydrochloride.

As used herein, the term "pharmaceutically acceptable salt" includes salts with appropriate acids are, for example, inorganic acids, such as a hydrohalic acid, e.g. hydrochloric, hydrobromic, and sulfuric acid, nitric acid, phosphoric acid; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic acids. The preferred salt within the scope of the invention is the hydrochloride acid addition salt.

The active ingredient, for example, nebivolol or a pharmaceutically acceptable salt thereof, is typically present within the composition at a concentration of about 0.5% by weight to about 10% by weight of the composition. The final concentration of active ingredient is selected based on the required dosage of the active ingredient.

The active ingredient used in the compositions of the present invention can be unmicronized. As used herein, the term "unmicronized" refers to solid particles of nebivolol or pharmaceutically acceptable salts, preferably the hydrochloride salt which exhibit a specific surface area of less than about $23 \times 10^3$ cm$^2$/g ($2.3 \times 10^3$ m$^2$/kg).

Although the compositions of the present invention do not require that the active ingredient be micronized, the active ingredient can be micronized prior to formulation in a composition of the present invention.

Wetting Agent

As described above, the compositions of the present invention comprise a wetting agent. As used herein, the term "wetting agent" means a compound used to aid in attaining intimate contact between solid particles and liquids.

Useful wetting agents include by way of example and without limitation, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters or polysorbates (e.g., TWEEN®), polyethylene glycols, polyoxyethylene stearates, phosphates, sodium lauryl sulphate, poloxamer, sodium dodecylsulfate, carboxymethylcellulose calcium, carboxymethylcellulose sodium, methylcellulose, hydroxyethylcellulose, hydroxyl propylcellulose, hydroxypropylmethylcellulose phthalate, noncrystalline cellulose, magnesium aluminum silicate, triethanolamine, polyvinyl alcohol, and polyvinylpyrrolidone (or PVP). Tyloxapol (a nonionic liquid polymer of the alkyl aryl polyether alcohol type, also known as superinone or triton) is another useful wetting agent, combinations thereof and other such materials known to those of ordinary skill in the art.

Although colloidal silicon dioxide is sometimes found to exhibit wetting agent properties, when used in the compositions of the present invention, the colloidal silicon dioxide is acting as a glidant (see discussion below) and not as a wetting agent.

In a particularly preferred embodiment the wetting agent is a polysorbate, more preferably polysorbate 80. The preferred weight range of the polysorbate is from about 0.01% to about 0.04% by weight with about 0.03% being particularly preferred. The ratio (w/w) of wetting agent to active ingredient must always be less than 0.025.

Additional Components/Excipients

The compositions of the present invention can also contain one or more pharmaceutically acceptable adjuvants or excipients. The pharmaceutically acceptable excipients for use in the compositions of the present invention include, but are not limited to, fillers, glidants, lubricants, diluents, binders, disintegrants, carriers, colorants, coatings and the like, and mixtures thereof, that are typically used in the art for preparation of oral solid dosage forms.

As used herein, the term "diluent" or "filler" is intended to mean inert substances used as fillers to create the desired bulk, flow properties, and compression characteristics in the preparation of tablets and capsules. Useful fillers or diluents may be inert fillers, either water soluble or water insoluble and selected from those typically used in the pharmaceutical art for oral solid dosage forms. Suitable fillers include, but are not limited to, calcium carbonate, dicalcium phosphate, tricalcium phosphate, microcrystalline cellulose, monosaccharide, disaccharides, polyhydric alcohols, sucrose, dextrose, lactose, mannitol, sorbitol, alone or mixtures thereof and the like or mixtures thereof. Particularly preferred fillers within the scope of the invention are lactose, even more preferred lactose monohydrate and spray dried mixtures of microcrystalline cellulose and lactose e.g. sold under the trade name Microcelac® These fillers can be used alone or in combination. The preferred percentage by weight range either alone or in combination within the scope of the invention is about 20% by weight to about 80% by weight.

As used herein, the term "lubricant" is intended to mean substances used in tablet formulations to reduce friction during tablet compression. Useful lubricants include, by way of example and without limitation, calcium stearate, magnesium stearate, mineral oil, stearic acid, zinc stearate, combinations thereof and other such materials known to those of ordinary skill in the art. The preferred lubricant is magnesium stearate. The preferred weight range of magnesium stearate is from about 0.25% to about 2% by weight with about 0.5% being particularly preferred.

As used herein, the term "disintegrant" is intended to mean a compound used in solid dosage forms to promote the disruption of the solid mass into smaller particles which are more readily dispersed or dissolved. Useful disintegrants include, by way of example and without limitation, starches such as corn starch, potato starch, pre-gelatinized and modified starched thereof, sweeteners, clays, such as bentonite, microcrystalline cellulose (e.g. Avicel®), Crospovidone, carsium (e.g. Amberlite), alginates, sodium starch glycolate, gums such as agar, guar, locust bean, karaya, pectin, tragacanth, combinations thereof and other such materials known to those of ordinary skill in the art. The preferred disintegrants are Croscarmellose sodium and Corn starch either alone or in combination. The preferred weight ranges of these disintegrants alone are from about 2% to about 30%. Corn starch is optimally used at about 20% by weight and the Croscarmellose sodium within the range of about 2% to about 3% by weight of the composition.

As used herein, the term "binders" is intended to mean substances used to cause adhesion of powder particles in tablet granulations. Useful binders within the scope of the invention include the following non limiting examples e.g. starch, poly(ethylene glycol), guar gum, polysaccharide, bentonites, sugars, invert sugars, poloxamers (PLURONIC F68®, PLURONIC F127®), collagen, albumin, celluloses e.g. hydroxypropylmethylcellulose, combinations thereof and the like. Other binders include, for example, poly(propylene glycol), polyoxyethylene-polypropylene copolymer, polyethylene ester, polyethylene sorbitan ester, poly(ethylene oxide), microcrystalline cellulose, polyvinylpyrrolidone, combinations thereof and other such materials known to those of ordinary skill in the art. The preferred binder within the scope of the invention is hydroxypropylmethylcellulose. The preferred weight range of hydroxypropylmethylcellulose is from about 1% to about 4% by weight of the composition.

As used herein, the term "glidant" is intended to mean agents used in tablet and capsule formulations to improve flow-properties during tablet compression and to produce an anti-caking effect. Useful glidants may be any glidant typically used in the pharmaceutical art for oral solid dosage forms. Examples include, but are not limited to, colloidal silicon dioxide. The preferred glidant is colloidal silicon dioxide. The preferred weight range is from about 0.1% to about 2.0% by weight, based on the total weight of the composition.

Most of the above excipients are described in detail in, e.g., Howard C. Ansel et al., Pharmaceutical Dosage Forms and Drug Delivery Systems, (7th Ed. 1999); Alfonso R and Gennaro et al., Remington: The Science and Practice of Pharmacy, (20th Ed. 2000); and A; Kibbe, Handbook of Pharmaceutical Excipients, (3rd Ed. 2000), both of which are incorporated by reference herein.

Process for Production

Oral administration is the generally preferred route for administration of compositions within the scope of the invention since this route is particularly convenient and acceptable to patients. Accordingly, a preferred embodiment of the present invention provides tablets prepared from the compositions of the present invention.

Tablets according to the present invention may be produced by any standard tabletting technique, e.g. by wet granulation, dry granulation or direct compression as described in Lachman and Liebermann second edition. For example, by granulating the active component with or without an excipient, followed by addition of any other excipient(s) and then compression to form a tablet. The tablets are preferably made by wet granulation methods as are known in the art; Lachman & Lieberman, Pharmaceutical Dosage Forms: Tablets, Vol 2, second edition, 1990, page 7. This may be carried out by blending the active ingredient with one or more pharmaceutically acceptable adjuvants, adding a granulation liquid to form a granulate, optionally drying the granulate and compressing the material into tablets.

As noted above, a preferred embodiment of the present invention provides a pharmaceutical composition comprising nebivolol or a pharmaceutically acceptable salt thereof. In general effective doses for the treatment of coronary vascular disorders in humans and in particular, conditions associated with the treatment of mild to moderate essential hypertension, will lie in the range of about 0.1 to about 50 mg, most preferably about 1 to about 10 mg, for example about 5 mg of the active ingredient per unit dose which could be administered in single or divided doses, for example, 1 to 4 times per day. The safe and effective amount of the compositions of the present invention will vary depending on the age and physical condition of the patient being treated, the severity of the condition, the duration of treatment and other factors within the purview of the skilled physician.

The present invention can be explained in the following non limiting examples. One of ordinary skill in the art will understand how to vary the exemplified preparations to obtain the desired results. Further, the following examples are given for the purpose of illustrating the present invention and should not be considered as limiting the scope or spirit of the invention in any way.

EXAMPLES

Example 1

| No | Item | Mg | % |
|---|---|---|---|
| 1 | Nebivolol Hydrochloride | 5.45 | 2.37 |
| 2 | Lactose Monohydrate (impalpable #100) | 100.00 | 43.48 |
| 3 | Croscarmellose Sodium NF | 6.90 | 3.00 |
| 4 | Corn Starch NF | 46.00 | 20.00 |
| 5 | Polysorbate 80 | 0.07 | 0.03 |
| 6 | Hydroxyproplymethylcellulose | 4.60 | 2.00 |
| 7 | Purified Water | N/a | |
| 8 | Purified Water | N/a | |
| 9 | Spray dried Microcrystalline Cellulose & Lactose monohydrate (Microcelac 100) | 60.63 | 26.36 |
| 10 | Croscarmellose sodium NF | 4.60 | 2.00 |

Tablet Composition

-continued

| Tablet Composition | | | |
|---|---|---|---|
| No | Item | Mg | % |
| 11 | Colloidal Silicon Dioxide | 0.60 | 0.26 |
| 12 | Magnesium Stearate | 1.15 | 0.50 |

Method of Manufacture
a) Mix Item #7 with Item#5 and dissolve Item#6 into Item#7 till clear solution is obtained. This is the binder solution.
b) Pass Item #1-4 thru a #20 mesh. Mix for 2 minutes in the Fluid Bed Dryer.
c) Spray binder solution onto the blend from step b).
d) Dry the material from step c)
e) Pass dried granules from step d) thru a #20 mesh.
f) The dried granules from step e) can optionally be milled thru a 039R Comill.
g) Blend screened granules of step f) with Items #9-11 (prescreen excipients thru a #20 mesh) and Blend in a v-blender.
h) Prescreen Item #12 thru a #30 mesh and blend for 3 minutes in a suitable v-blender.
i) Compress the blend from step h).

Example 2

Dissolution testing of compositions prepared in accordance with example 1 was compared with reference samples of NEBILET® 5 mg (marketed by A. Menarini Pharmaceuticals UK Ltd).
Dissolution Test
The test method and parameters are described more fully below. The time points for sampling were at 15 minutes, 30 minutes and 45 minutes. 900 ml of 0.1 M Hydrochloric acid was used as the test solution. The aliquots of nebivolol sampled at each time point were injected into a standard High Performance Liquid Chromatography column equipped with an Ultra Violet detector. The samples were quantified against a standard of known concentration based on the sample versus standard peak response. The dissolution specification required was at least 75% after 45 minutes.

| Dissolution Equipment and Parameters | |
|---|---|
| Method: | Apparatus II (Paddles) |
| Speed: | 50 rpm |
| Dissolution Medium: | 0.1N HCl |
| Volume: | 900 mL |
| Run Time: | 45 minutes |
| Temperature: | 37° C. ± 0.5° C. |
| HPLC Equipment and Parameters | |
| Column: | Ace 3 Phenyl, 150 mm × 4.6 mm, 3 µm |
| Flow Rate: | 1.2 mL/min |
| Injection Volume: | 40 µL |
| Run Time: | 15 minutes |
| Wavelength: | 283 nm |
| Column Temperature: | 30° C. |
| Mobile Phase: | *Buffer solution: Acetonitrile (72:28) |
| | *Buffer solution preparation: Dissolve 3.4 g of tetra butyl ammonium hydrogen sulfate (tetrabutyl ammonium bisulfate) and 0.3 mL of diethylamine in 1000 mL of water. Mix well. |
| Diluting Solvent: | Methanol:Dissolution medium (50:50) |
| Needle Wash: | Water:Acetonitrile (50:50) |
| Blank: | Dissolution medium |

Standard Preparation
A. Standard Stock Solution
Prepare in duplicate. Accurately weigh about 24 mg of Nebivolol HCl (equivalent to 22 mg of Nebivolol) into a 100 mL volumetric flask. Add about 60 mL of diluting solvent and sonicate with occasional swirling for one minute or until dissolved. Dilute to volume with diluting solvent and mix well (conc.≈220 µg/mL of Nebivolol).
B. Standard Working Solution (for 5 mg Tablet)
Pipet 5.0 mL of Standard Stock Solution into a 200 mL volumetric flask. Dilute to volume with dissolution medium and mix well (conc.≈5.5 µg/mL of Nebivolol).
Sample Preparation
Place 900 ml of dissolution medium into each of the six dissolution vessels and equilibrate the medium to 37° C.±0.5° C. Preset the paddle speed to 50 rpm. Lower the paddles into the dissolution medium (paddles should not be rotating). Place one tablet into each of the six vessels allowing them to sink before starting the apparatus. At 45 minutes, withdraw 10 mL of sample from each vessel using probes from a zone midway between the surface of the dissolution medium and the top of the rotating blade, not less than 1 cm from the vessel wall. The solution is filtered immediately.
Chromatographic Procedure and System Suitability
Inject blank to ensure the baseline is clean and stable.
Inject Standard Working Solution 1 five times. Calculate the relative standard deviation (RSD), tailing factor (T), and number of theoretical plates (N). The RSD is not more than 2.0%, T is not more than 1.5 and N is not less than 10000.
Inject Standard Working Solution 2, blank and Sample Working Solutions once each.
Inject Standard Working Solution 1 once after every six sample injections and once at the end of the run.
Calculation $$\% \ LC \ \text{Dissolved} = \frac{A_{SPL}}{A_{STD}} \times W_{STD} \times \frac{DF}{LC} \times \frac{405.43}{441.89} \times 100$$

Where:
$A_{SPL}$=Peak area of Nebivolol in the sample solution
$A_{STD}$=Average peak area of Nebivolol in the standard
$W_{STD}$=Weight of Nebivolol HCl in mg (corrected for "as-is" potency)
DF=Dilution Factor
  =Standard Dilution
    Sample Dilution
LC=Label claim of Nebivolol in mg/tablet
405.43=Molecular Weight of Nebivolol
441.89=Molecular Weight of Nebivolol HCl
Results 5 mg Tablet from Example 1

| Tablet # | 15 min | 30 min | 45 min |
|---|---|---|---|
| 1 | 88.54% | 98.27% | 99.04% |
| 2 | 89.43% | 98.01% | 100.30% |
| 3 | 87.40% | 97.04% | 99.81% |
| 4 | 89.46% | 98.89% | 101.10% |
| 5 | 94.32% | 101.92% | 103.16% |
| 6 | 96.49% | 100.92% | 101.47% |
| Average | 90.94% | 99.18% | 100.81% |

5 mg NEBILET® (Marketed by A. Menarini Pharmaceuticals UK Ltd)

| Tablet # | 15 min | 30 min | 45 min |
|---|---|---|---|
| 1 | 84.59% | 96.15% | 98.38% |
| 2 | 84.18% | 95.88% | 99.18% |
| 3 | 84.68% | 97.43% | 99.94% |
| 4 | 85.41% | 96.72% | 98.56% |
| 5 | 87.48% | 96.32% | 98.10% |
| 6 | 85.60% | 95.15% | 96.54% |
| Average | 85.32% | 96.28% | 98.45% |

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A pharmaceutical composition for oral administration comprising an active ingredient and a wetting agent, wherein the pharmaceutical composition is a solid pharmaceutical composition in the form of a tablet, wherein the active ingredient is nebivolol hydrochloride, the wetting agent is polysorbate 80, the pharmaceutical composition comprises, on a weight percentage basis, from about 0.01% to about 0.04% of the wetting agent and from about 0.5% to about 10% of the active ingredient, and the ratio (w/w) of wetting agent to active ingredient is less than 0.025,
wherein the composition further comprises from about 20% to about 80% of a spray dried mixture of microcrystalline cellulose and lactose and/or lactose monohydrate, from about 1% to about 4% of hydroxypropylmethylcellulose, from about 2% to about 30% of corn starch and/or croscarmellose sodium, from about 0.25% to about 2% of magnesium stearate and from about 0.1% to about 2% of colloidal silicon dioxide, and
wherein the active ingredient is added to the pharmaceutical composition in the form of unmicronized solid particles having a specific surface area of less than $23 \times 10^3$ cm$^2$/g.

2. The pharmaceutical composition of claim 1 comprising, on a weight percentage basis, about 2.37% of nebivolol hydrochloride, about 0.03% of polysorbate 80, about 26.36% of a spray dried mixture of microcrystalline cellulose and lactose, about 43.48% of lactose monohydrate, about 2% of hydroxypropylmethylcellulose, about 20% of corn starch, about 5% of croscarmellose sodium, about 0.5% of magnesium stearate and about 0.26% of colloidal silicon dioxide.

3. The pharmaceutical composition of claim 1, wherein the tablet exhibits a dissolution of at least 75% after 15 minutes.

4. The pharmaceutical composition of claim 1 consisting essentially of, on a weight percentage basis, from about 0.5% to about 10% of nebivolol hydrochloride, from about 0.01% to about 0.04% of polysorbate 80, from about 20% to about 80% of a spray dried mixture of microcrystalline cellulose and lactose and/or lactose monohydrate, from about 1% to about 4% of hydroxypropylmethylcellulose, from about 2% to about 30% of corn starch and/or croscarmellose sodium, from about 0.25% to about 2% of magnesium stearate and from about 0.1% to about 2% of colloidal silicon dioxide.

5. The pharmaceutical composition of claim 1 consisting of, on a weight percentage basis, about 2.37% of nebivolol hydrochloride, about 0.03% of polysorbate 80, about 26.36% of a spray dried mixture of microcrystalline cellulose and lactose, about 43.48% of lactose monohydrate, about 2% of hydroxypropylmethylcellulose, about 20% of corn starch about 5% of croscarmellose sodium, about 0.5% of magnesium stearate and about 0.26% of colloidal silicon dioxide.

* * * * *